Figure 2:
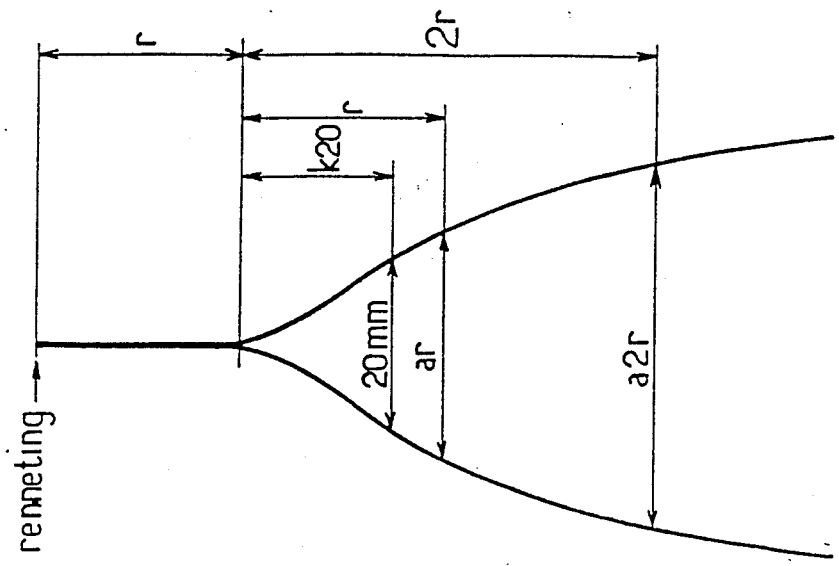

United States Patent [19]

Serpelloni

[11] Patent Number: 5,009,914
[45] Date of Patent: Apr. 23, 1991

[54] PROCESS FOR CONFERRING CHEESE MAKING PROPERTIES ON OVERHEATED MILKS FOR THE MANUFACTURE OF RENNETED CHEESES

[75] Inventor: Michel Serpelloni, Beuvry les Bethune, France

[73] Assignee: Roquette Freres, Lestrem, France

[21] Appl. No.: 365,571

[22] Filed: Jun. 14, 1989

[30] Foreign Application Priority Data

Jun. 14, 1988 [FR] France ................. 88 07932

[51] Int. Cl.⁵ .............................................. A23C 19/04
[52] U.S. Cl. .................................... 426/582; 426/36; 426/39
[58] Field of Search ................. 426/580, 582, 36, 39

[56] References Cited

U.S. PATENT DOCUMENTS 3,539,363 11/1970 Morgan et al. ................. 426/36
4,388,329 6/1983 Buhler et al. .................. 426/582
4,713,254 12/1987 CHilds et al. .................. 426/582

FOREIGN PATENT DOCUMENTS

WO85/00501 2/1985 World Int. Prop. O. .

Primary Examiner—Donald E. Czaja
Assistant Examiner—Helen Pratt
Attorney, Agent, or Firm—Fleit, Jacobson, Cohn, Price, Holman & Stern

[57] ABSTRACT

For conferring cheese making properties on milk before or after a heat treatment carried out at temperatures above 78° C., which milk is intended for the manufacture of renneted cheeses, an effective quantity, for example 5 to 200 g/hl, of acidogenic agent, for example glucono-delta-lactone, is added before or after the said heat treatment. Application to the manufacture of renneted cheeses from milks which have been heated to a high temperature.

5 Claims, 1 Drawing Sheet

PROCESS FOR CONFERRING CHEESE MAKING PROPERTIES ON OVERHEATED MILKS FOR THE MANUFACTURE OF RENNETED CHEESES

The present invention relates to a new process for conferring cheese making properties on milks before or after they have been heat treated at temperatures above 78° C., with a view to the manufacture of renneted cheeses.

In the context of this invention, the term "renneted cheeses" is used in accordance with the classification given in "LE FROMAGE" brought out by André ECK in Technique et Documentation (Lavoisier) Paris (1984), in particular pages 220–221, to denote all those cheeses which are obtained from curds produced by the action of coagulating enzymes. More particularly, it denotes soft cheeses (Camembert, Carré de l'Est, Brie, Munster . . . ), pressed cooked cheeses (Gruyère, Emmentaler, Comté, Beaufort, Grana . . . ), pressed uncooked or semi-cooked cheeses (Port-Salut, Tomme, Cantal, Gouda, Edam, Tilsiter, Saint-Paulin, Reblochon, Morbier, Cheddar . . . ) and blue type marbled cheeses (Danish, Bavarian, Gex, Bresse, Fourmes, Gorgonzola, Stilton, Roquefort . . . ).

According to "LE FROMAGE" by André ECK cited above, pages 149 to 157, the "cheese making properties of a milk" are generally understood to be its capacity subsequently to yield, for example by the action of rennet, a coagulum:

which is sufficiently firm to withstand the mechanical operations conventionally carried out in the manufacture of cheese, such as cutting, stirring and moulding, within the time normally required for such industrial processes, which has a sufficiently low friability to prevent fines from being carried away by the whey or lactoserum when the cheese is being drained, these fines consisting mainly of proteins and fats, and which drain in the correct manner so as to give rise first to a curd and then to a cheese whose dry matter content is compatible with the characteristics required in the manufactured cheese.

It is known that the cheese yield may be increased by treating milk intended for cheese-making at temperatures above 78° C. and that it is of interest for hygienic reasons to be able to subject milk to such temperatures (Michael P. Doyle and coworkers, Applied and Environmental Microbiology, July 1987, pages 1433-1438: "Survival of *Listeria monocytogenes* in Milk during High-Temperature, Short-Time Pasteurization".

This increase in yield results from the coprecipitation of soluble proteins with the casein micellae by the process described hereinafter.

It is well known that heat treatments, in particular at temperatures above 78° C., impair the capacity of milk for being converted into cheese. When milk is heated to a temperature above 78° C. (upper limit of temperatures at which milk is conventionally heat treated), two main phenomena occur:

1. An interaction between the proteins of the whey (alpha lactalbumin and beta lactoglobulin) and the caseins by hydrophobic bonds and especially by an activation of the sulphhydryl groups SH which give rise to a complex between the beta lactoglobulin and K (Kappa) casein, the steric hindrance of which complex being such that it opposes the action of the coagulating enzyme, chymosine.

As a result, coagulation becomes more difficult and generally takes place more slowly than is normal. This has the following effects in practice:

increase in the setting time and increase in the hardening time, i.e. the time required for obtaining a coagulum of standard hardness.

2. Substantial reduction in the concentration of soluble calcium, so that formation of the bonds between the micellae required to take place for the formation and hardening of the gel becomes more difficult.

The gel is then generally more fragile (more friable), with the result that there is a considerable increase in the loss of material (fine particles) into the whey at the curd-formation stage.

It has already been attempted to overcome the above-mentioned drawbacks by applying various corrections to thus treated milks, namely: enrichment in proteins, retention of whey proteins by ultrafiltration (total concentration—FETA Patent Application WO 85 501), lowering of the renneting pH and increase in the soluble calcium content.

These attempts have been carried out mainly on milks which have been subjected to heat treatments in the course of their conversion into powdered milk. In fact, if these milks could regain their entire cheese-making capacity after having been reconstituted, they could be more widely used for cheese making and they would thus be able to conform to certain requirements of rationalisation in the production of milk and to be free from certain climatic limitations.

It is, however, found that the corrections contemplated for restoring the cheese making properties of these reconstituted milks have their limits and they have not been able to satisfy all the requirements of the cheese producing industry, particularly on account of the loss of material in the whey and the difficulties in draining. The use of milk reconstituted from powdered milk for producing traditional cheeses has only been achieved, if at all, by means of certain special techniques, such as in particular the technique known as "simplified instantaneous coagulation" (CIS = Coagulation Instantanée Simplifiée) which differ from traditional methods employed in the manufacture of renneted cheeses.

It is also known that cheese producers have used some of these means for correcting the mediocre cheese making capacity of certain milks used in traditional cheese making, with a view to obtaining a clotted product or coagulum suitable for cheese making [Y. Amram & coworkers, Rev. Lait. Fr. (1982) 404, 53–57 and Ichilczyk-Leone Y. and coworkers, Rev. Lait. Fr. (1981) 401, 7].

The envisaged corrections, however, have not succeeded up to the present time in restoring the cheese making properties of milks heated to high temperatures (above 78° C.) without major disadvantages or without resort to unconventional manufacturing techniques, so that these heat treatments could not be used for increasing the yields in conventional production processes.

In this context, therefore, other means have hitherto been employed for increasing the yield, namely: recovery of the whey proteins by ultrafiltration or by thermal precipitation with reintroduction of these proteins into the milk or curd.

Even if certain results have been obtained, however, particularly with milks heated to temperatures above 78° C., the excessively high protein concentration renders the manufacture of traditional renneted cheeses difficult.

It is also known in the traditional art that increasing the protein concentration of milk, either by ultrafiltration or simply by the addition of certain milk proteins, enables the firmness of the gels to be improved; but this is generally achieved at the expense of a reduction in the speed of clotting of the milk and hence an increase in the setting time, draining of the curd becoming more difficult.

It is also known that a lowering of the pH at which renneting is carried out enables, while reducing the stability of the casein micellae, to increase the speed of coagulation and the firmness of the coagulum; but the criteria for the conventional method of cheese manufacture do not allow the renneting pH to be reduced much below the conventional standards. Such a modification would in fact seriously affect the quality of the product obtained, in particular due to excessive demineralization of the curd. Further, an excessive lowering of the pH for renneting would increase the friability of the gels, which in turn would cause considerable losses of material into the whey when the curd is drained in the vat.

It is also known that the setting time may be reduced and the speed with which the coagulum becomes firm may be increased by the addition of calcium salts, in particular calcium chloride ($CaCl_2$). The addition of too large a quantity of $CaCl_2$, however, has a deleterious effect on the organoleptic properties of cheeses, in particular by increasing the bitterness (Charles ALAIS, "Science du Lait" (1984), pages 647 and 669). The amount of $CaCl_2$ added must therefore be limited, but that correction currently used is not always sufficient to overcome the disadvantages mentioned above.

It is thus found that the proposed corrections have not up to now succeeded in restoring the cheese making properties of milks heated to high temperatures (above 78° C.) except at the expense of major disadvantages or the use of unconventional manufacturing methods.

In conclusion, none of the existing solutions is able to overcome all the difficulties inherent in the use of high temperature treated milks, nor can cheeses, and more particularly renneted cheeses, having properties corresponding in all respects to those of cheeses produced from conventionally heat treated milk, be obtained by traditional cheese making processes from these overheated milks with all the benefits which are associated with these milks.

It is therefore an object of the present invention to overcome the drawbacks of the prior art and provide a new process for conferring cheese making properties on milks before or after their heat treatment at temperatures above 78° C. for the purpose of manufacturing renneted cheeses without employing novel cheese producing techniques.

It is to the credit of the Applicants that it was surprisingly found that the addition of an acidogenic agent to these milks can confer cheese making properties on them without deleteriously affecting the later stages in the manufacture of renneted cheeses (ripening, renneting, coagulation, cutting, stirring, refining, possibly pressing, heating, cheddarization, etc.) or the organoleptic properties of the end products.

Consequently, the process according to the invention adapted for conferring cheese making properties on a milk before or after its heat treatment at a temperature above 78° C., which milk is intended for the manufacture of renneted cheeses, is characterized in that it consists of adding to the milk an effective quantity of an acidogenic agent before or after said heat treatment.

The improvement obtained by the addition of an acidogenic agent to milk before or after such heat treatment enables in particular the cheese yield to be substantially increased, which is an economical advantage greatly appreciated by the man of the art.

The milk used according to the invention is a nonreconstituted milk of any origin; it may be raw or it may have been subjected to a prior heat treatment at a temperature not exceeding 78° C. and possibly standardised in its fat content and/or protein content and/or mineral content; it may even have been concentrated by any suitable means, in particular by ultrafiltration.

According to the invention, the heat treatment of the milk at temperatures above 78° C. is preferably chosen from the group of heat treatments carried out at temperatures from 78° C. to 110° C., in particular from 80° to 90° C., the duration of this treatment being generally from several seconds to one minute. The heat treatment may in particular be a type of pasteurization normally carried out for 15 to 40 seconds, depending on the storage period characteristic of the particular manufacturing unit.

An acidogenic agent is understood in this context to be any substance capable of progressively generating an acid in the milk, either by solubilization or by release of acid.

The substances capable of progressively generating an acid in milk by solubilization include in particular lactones such as gluconolactones and glucoheptonolactones and the like and/or mixtures thereof which progressively hydrolyse to the corresponding acid in an aqueous medium.

Examples of substances capable of progressively generating an acid in milk by release include acids fixed on a solubilising support or released by delayed action.

The acidogenic agent may be added in the form of a powder or a solution, as desired.

When the acidogenic agent is added in the form of a powder, its dispersion in the milk and its solubilization may be effected by any suitable stirring means.

When it is preferred to add the acidogenic agent in the form of a solution, i.e. a solution in milk or water, the solution is preferably prepared immediately before use in order to preserve the acidogenic character of the agent as defined above.

In practice, and bearing in mind the particular characteristics of each production line for renneted cheeses, the technician will determine the best moment for introducing the acidogenic agent into the milk before coagulation.

The acidogenic agent may, for example, be introduced into the raw milk, before or after a first treatment of pasteurization optionally carried out, before or after the heat treatment within the meaning of the invention, i.e. a heat treatment at a temperature above 78° C.

Other variations could, of course, equally well be envisaged.

It would, however, generally appear to be most advantageous to introduce the acidogenic agent into the milk after the heat treatment carried out above 78° C.

The quantity of acidogenic agent used for the purpose of this invention is advantageously from 3 to 500 g/hl of milk, preferably from 5 to 200 g/hl of milk and still more preferably from 10 to 100 g/hl of milk.

In certain cases, it would be preferable to select an amount of acidogenic agent such that the milk will have the required pH for renneting after hydrolysis of the acidogenic agent. This procedure enables the lactifying enzymes having an acidifying role to be replaced during the phase of maturation of the milk so that the pH can be perfectly controlled during this phase. The advantages obtained for the manufacture of cheese by using milk which is heat treated within the meaning of the invention can be combined with the advantages obtained from this replacement of the lactic enzymes, which improves the possibility of automation of the production lines for renneted cheeses.

The preferred acidogenic agent used for this invention is glucono-delta-lactone (GDL). In addition to the advantages mentioned above for acidogenic agents, its excellent solubility in the aqueous media and its controlled kinetics of hydrolysis render it perfectly suited to the requirements of renneted cheese manufacture. Further, the Applicants have surprisingly found that virtually no gluconic acid resulting from the hydrolysis of GDL is left in the finished product.

Lastly, according to the invention, other additives may be introduced into the milk in addition to the acidogenic agent, in particular for the purpose of standardizing the protein content and mineral content of the milk, e.g. the calcium content.

The invention will be better understood with the aid of the Examples which follow and which relate to advantageous embodiments.

The cheese making capacity of milks may be asessed by means of various instruments which measure the formation and development of gels in the course of the coagulation [paper by the INSTITUT DU GRUYERE (paper I.T.G. ZO 84.01B)]. Among these may be mentioned the device marketed under the name FORMAGRAPH (by FOSS ELECTRIC) which is used in various research laboratories and dairy colleges. This type of device may be used to determine whether the coagulum is sufficiently firm for the requirements of a traditional cheese making process.

Figure 1:
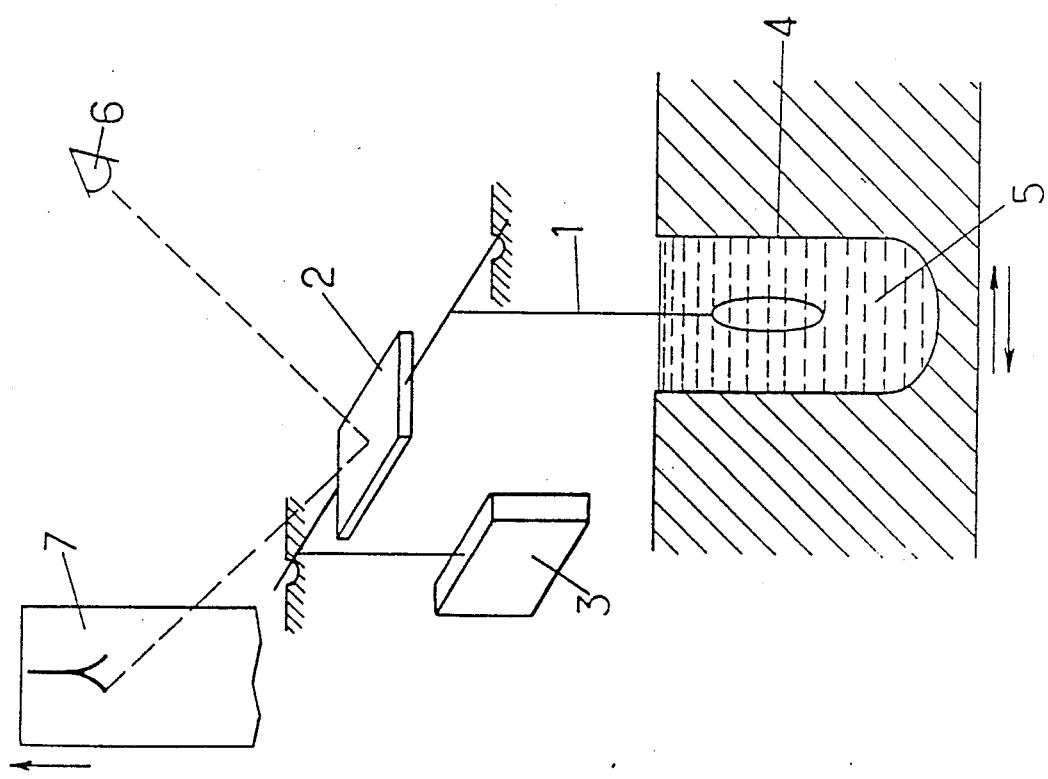

Practical information on this type of apparatus is given in the abovementioned paper I.T.G. ZO 84.01B. The principle of its operation is illustrated schematically in FIG. 1 of the attached drawings.

A balancing device or cross arm 1 connected to a mirror 2 and balanced by a counterweight 3 is immersed in a micro-vat 4 (10 ml) containing the milk 5 whose cheese making properties are to be assessed.

The micro-vat 4 is subjected to a reciprocating movement in the horizontal direction. When the milk coagulates, the balancing device 1 is carried along by the gel which is in the process of formation. A beam of light 6 is directed on the mirror 2 at the end of each horizontal displacement of the micro-vat 4 so that the oscillation of the balancing device 1 can be recorded on a photosensitive paper 7 as a record of the progress of coagulation of the milk.

The graph obtained, which is shown in FIG. 2 of the attached drawing, serves to characterize the cheese making capacity of a milk mainly from the following parameters:

r: coagulation time (correlated with the setting time) in mm;

ar: distance in mm between the two arms of the graph after one r ($1 \times r$);

a2r: distance after $2 \times r$;

k20: time required for the distance between the arms to reach 20 mm.

Parameters r and k20 are a measure of the speed of coagulation and ar and a2r reflect the firmness of the gel.

Good cheese making capacity of a milk may be characterized by way of example and in accordance with the art by the following parameters:

for a long coagulation time:
  r=35 to 40 mm
  k20=20 to 30 mm
  ar>30 mm
  a2r>40 mm for a short coagulation time:
  r=20 to 35 mm
  k20=12 to 20 mm
  ar>29 mm
  a2r>38 mm.

In the Examples which follow, the values for r, k20, ar and a2r are given in mm.

EXAMPLE 1 Control experiment

Cheese making capacity of a milk heat treated at 85° C. for 20 seconds

A raw bulk milk is pasteurized at 85° C. for 20 seconds, cooled to 10° C., standardized to a fat content of 30 g/l and a protein nitrogen content of 34 g/l and then 0.075 g/l of anhydrous $CaCl_2$ is added.

A sufficient quantity of lactic bacteria is added to the milk which has been thus treated (day J-1). After maturation for 16 h. at 13° C., a pH of 6.45 is obtained at the moment of renneting.

The milk is then taken up on day J and heated to 38° C. (renneting temperature) and 0.035 g of anhydrous $CaCl_2$ are added. Renneting is carried out by the addition of rennet containing 520 mg/l of active chymosine (Trade Mark BOLL) diluted to 2.5%, used in an amount equivalent to 25 ml of rennet extract per 100 liters of milk.

The process of coagulation is followed on a FORMAGRAPH (marketed by FOSS ELECTRIC) and the following results are obtained: renneting pH: 6.45
  r=43
  k20=33
  ar=25
  a2r=37.

The coagulation parameters are those corresponding to the manufacture of a stabilized type of cheese.

It is found that the gel is formed too slowly and is not sufficiently firm for the formation of a normal curd (too soft).

The milk used as starting material thus has not sufficient cheese making capacity for the manufacture of products in this technology.

EXAMPLE 2

Correction of the cheese making property of a milk which has been heat treated at 85° C. for 20 seconds by the addition of glucono-delta-lactone The same raw bulk milk as that used in Example 1 heat treated at 85° C. for 20 seconds is used for this experiment. The milk, being identical to that of Example 1, has thus been standardized to a fat content of 30 g/l and a protein nitrogen content of 34 g/1 and adjusted by the addition of 0.075 g/l of $CaCl_2$. This standardized milk is then cooled to 10° C.

In constrast to Example 1, no lactic acid bacteria are introduced into this standardized milk but 0.38 g of glucono-delta-lactone are added per liter of milk so that a pH of 6.45 can be obtained the following day for renneting.

The milk thus prepared is taken up on day J and heated to 38° C. (renneting temperature), and 0.035 g of anhydrous $CaCl_2$ is added. Renneting is carried out as in Example 1 by the addition of rennet containing 520 mg/l of active chymosine (Trade Mark BOLL) diluted to 2.5% and used in a dose equivalent to 25 ml of rennet extract per 100 liters of milk.

The process of coagulation is followed on a FORMAGRAPH (FOSS ELECTRIC) and the following results are obtained:
 renneting pH: 6.45
 r=39.0
 k20=27.5
 ar=30.0
 a2r=40.5.

The cheese making capacity of the gel obtained in this case is found to be improved so that coagulation may be carried out under normal manufacturing conditions. The glucono-delta-lactone has thus been able to restore the cheese making capacity of this milk so that a sufficient level of performance for cheese production could be obtained.

EXAMPLE 3

Correction of the cheese making capacity of a protein-standardized milk by the addition of GDL A raw bulk milk is pasteurized at 85° C. for 20 seconds and then cooled to 10° C. and standardized to a fat content of 30 g/l and a protein nitrogen content of 33 g/l by the addition of 3 g/l of calcium caseinate, and 0.075 g/l of anhydrous $CaCl_2$ and 0.40 g of glucono-delta-lactone per liter of milk are added.

The milk treated as described above is kept overnight at 10° C. (day J-1). The quantity of GDL put into the process enables a renneting pH of 6.44 to be obtained from milk initially at pH 6.75.

The milk is taken up on day J and heated to 35° C. (renneting temperature) and 0.035 g of anhydrous $CaCl_2$ per liter of milk are added, as well as rennet containing 520 mg/l of active chymosine (Trade Mark BOLL) diluted to 2.5% and used in a dose equivalent to 25 ml of rennet extract per 100 liters of milk.

The process of coagulation is followed on a FORMAGRAPH (FOSS ELECTRIC) and the following results are obtained:
 r=32.0
 k20=17.0
 ar=32.0
 a2r=43.0.

This corresponds to a coagulum suitable for cheese making, for example by the technique used for stabilized cheese (or solubilized cheese of the Tomme Blanche type).

EXAMPLE 4

Correction of the cheese making capacity of a milk which has been heat treated at 82° C. by the addition of GDL A raw bulk milk is pasteurized at 82° C. for 20 seconds, then cooled to 10° C. and standardized to a fat content of 30.0 g/l and a protein nitrogen content of 32.5 g/l and 0.075 g/l of anhydrous $CaCl_2$ and 0.22 g of glu-cono-delta-lactone are added per liter of milk put into the process.

The milk treated as described above is kept (day J-1) for 1 night at 10° C. The quantity of GDL put into the process enables the renneting pH of 6.50 to be obtained.

The milk is taken up on day J and heated to 35° C. (renneting temperature) and 0.035 g of anhydrous $CaCl_2$ per liter of milk are added, as well as rennet containing 520 mg/l of active chymosine (Trade Mark BOLL) diluted to 2.5% and introduced in a dose equivalent to 25 ml of rennet extract per 100 liters of milk.

Coagulation is followed on a FORMAGRAPH (FOSS ELECTRIC) and the following results are obtained:
 r=35.0
 k20=22.5
 ar=31.0
 a2r=42.0.

This corresponds to a coagulum suitable for cheese making, for example by the technique for producing stabilized pressed cheese of the type of Tomme à croûte fleurie.

EXAMPLE 5

Correction of the cheese making capacity of a milk which has been heat treated at 85° C. for its conversion into a pressed cheese A raw bulk milk is pasteurized at 85° C. for 20 seconds, cooled to 10° C. and standardized to a fat content of 30 g/l and a protein nitrogen content of 34.5 g/l and 0.125 g/l of anhydrous $CaCl_2$ are added as well as 0.24 g of glucono-delta-lactone per liter of milk.

This treated milk is stored overnight (day J-1) at 10° C. The quantity of GDL put into the process enables the renneting pH of 6.50 to be obtained.

The milk is taken up on day J and heated to 33° C. (renneting temperature) and 0.035 g of anhydrous $CaCl_2$ per liter of milk are added, as well as rennet containing 520 mg/l of active chymosine (Trade Mark BOLL) diluted to 2.5% and introduced in a dose equivalent to 25 ml of rennet extract per 100 liter of milk.

The process of coagulation is followed on a formagraph (foss electric) and the following results are obtained:
 r=36.0
 k20=21.0
 ar=34.0
 a2r=44.5.

This corresponds to a coagulum suitable for cheese making, for example for the production of an uncooked, pressed cheese of the Saint-Paulin type.

EXAMPLE 6

Cheese making capacity of a milk which heat treated at 85° C. for 20 seconds with addition of GDL before this heat treatment 0.20 g/l of glucono-delta-lactone are added to raw bulk milk at pH 6.78 so that a renneting pH of 6.50 is subsequently obtained.

This milk is heat treated at 85° C. for 20 seconds and then cooled to 10° C. and standardized to a fat content of 30 g/l and a protein nitrogen content of 34.5 g/l and 0.075 g/l of anhydrous $CaCl_2$ are added.

The treated milk is stored (day J-1) for one night at 10° C.

The milk is taken up on day J and heated to 33° C. (renneting temperature) and 0.035 g of anhydrous $CaCl_2$ are added. Curdling is brought about by the addition of rennet containing 520 mg/1 of active chymosine (Trade Mark BOLL) diluted to 2.5% and introduced in a dose equivalent to 35 ml of rennet extract per 100 liters of milk.

The process of coagulation is followed on a formagraph (foss electric) and the following results are obtained:

r=23.0
k20=18.0
ar=29.0
a2r=43.5.

These results correspond to a coagulum suitable for cheese making by the processes employed for the manufacture of semi-cooked pressed cheese (of the Edam type).

EXAMPLE 7

Correction of the cheese making capacity of a milk heat treated at 85° C. for 20 seconds without ripening at a low temperature A raw bulk milk is kept at 4° C. for 5 hours. The milk is then treated at 85° C. for 20 seconds and standadized to a fat content of 33 g/1 and a protein nitrogen content of 34 g/1. This treated milk is cooled to 32° C. (renneting temperature) and 0.15 g/1 of anhydrous $CaCl_2$ and 2 g of glucono-delta-lactone per liter of milk are added.

When the pH of 6.55 is reached (several minutes after the introduction of GDL) renneting is carried out by the addition of rennet containing 520 mg/1 of active chymosine (Trade Mark BOLL) diluted to 2.5% and introduced in a dose equivalent to 40 ml of rennet extract per 100 liters of milk.

The process of coagulation is followed on a FORMAGRAPH (FOSS ELECTRIC) and the following results are obtained:

r=21.0
k20=15.0
ar=35.5
a2r=44.0.

These results demonstrate that the gel obtained is of good quality. They correspond to the restoration of the cheese making capacity of a milk which has been heat treated at 85° C. for 20 seconds for the manufacture of Cheddar type cheese.

EXAMPLE 8 comparison

Manufacture of a pressed cheese from a milk which has been heat treated at 72° C. for 20 seconds (by conventional technology)

A raw bulk milk is treated at 72° C. for 20 seconds and cooled to 10° C. This milk is standardized to a fat content of 32.5 g/1 and a protein nitrogen content of 36 g/1 and 0.20 g/1 of anhydrous $CaCl_2$ and 0.10 g of glucono-delta-lactone per liter of milk are added.

The milk is stored (day J-1) at 10° C. for 15 hours. Mesophile lactic enzymes (MA014 -EUROZYME) are then added (day J) to ensure acidification in the course of cheese production. Heating of the milk to 32° C. (renneting temperature) is carried out 2 hours after addition of the enzymes. Renneting is carried out by the addition of the same rennet as that used in the other Examples, at a dose of 30 ml per 100 liters of milk; the pH is then 6.58.

The setting time is 16 minutes and the hardening time 10 minutes, and the gel is then cut.

At this stage, the gel is sufficiently firm for the normal processes of cheese manufacture.

The latter is carried out by the conventional technology for the production of pressed cheeses:

stirring
first draining off of whey
removal of lactose
second draining off of whey
emptying of vat
moulding
pressing
acidification
salting in brine
drYing
maturing.

The cheese obtained has the following characteristics:

dry extract: 51.6%
fat content (based on dry extract): 46.5%
yield* 13.39 kg of cheese per 100 kg of milk.
*Yield corrected to standard dry extract (MAUBOIS yield).

This corresponds to the normal values for a pressed type of cheese.

The product obtained has the usual organoleptic properties characteristic of this cheese.

EXAMPLE 9

Manufacture of a pressed cheese from a milk treated at 85° C. for 20 seconds

A raw bulk milk is heat treated at 85° C. for 20 seconds and cooled to 10° C. This milk is standardized to a fat content of 32.5 g/1 and a protein nitrogen content of 36 g/1 and 0.20 g/1 of anhydrous $CaCl_2$ and 0.12 g of glucono-delta-lactone are added per liter of milk put into the process.

The milk is stored (day J-1) at 10° C. for 15 hours. Mesophile lactic enzymes (MA014 -EUROZYME) are then added (day J) to ensure acidification in the manufacture process. The milk is heated to 32° C. (renneting temperature) 2 hours after addition of the enzymes. Renneting is carried out by the addition of the same rennet as that used in the other Examples, using a dose of 30 ml per 100 liters of milk; the pH is then 6.53.

The setting time is 15 minutes and the hardening time 10 minutes, and the gel is then cut.

At this stage, the gel is sufficiently firm for the normal cheese making operations.

Manufacture of the cheese is carried out by the conventional technology for pressed cheeses:

stirring
first draining off of whey
removal of lactose
second draining off of whey
emptying of vat
prepressing
moulding
pressing
acidification
salting in brine
drying
maturing.

The cheese obtained has the following characteristics:

dry extract: 51.5%
fat content (based on dry extract): 47%
yield* 13.73 kg of cheese per 100 kg of milk.
*The yield corrected to a standard extract is greater than that obtained from the process of Example 8. The increase is about +2.5% for this manufacturing process.

This corresponds to normal values for a cheese of the pressed type.

The product obtained has good organoleptic qualities similar to those of a conventionally produced product.

I claim:

1. In a process for making cheese from milk, wherein curd is formed under the action of rennet on the milk, the said process comprising heat treating the milk at a temperature from 78° to 110° C., the improvement comprising incorporating into the milk an amount of from 0.03 to 5 g per liter of milk of an acidogenic agent selected from the group consisting of gluconolactones and glucoheptonolactones whereby cheese making properties are conferred on the milk.

2. A process according to claim 1, comprising heat treating the milk at a temperature from 80° to 90° C.

3. A process according to claim 1 comprising heat treating the milk from several seconds to 1 minute.

4. A process according to claim 1 wherein the amount of gluconolactone or of glucoheptonolactone is from 0.05 to 2 g/l of milk.

5. A process according to claim 1, wherein the amount of gluconolactone or of glucoheptonolactone is from 0.1 to 1 g/l of milk.

* * * * *